United States Patent
El-Khouri et al.

(10) Patent No.: US 10,426,722 B2
(45) Date of Patent: *Oct. 1, 2019

(54) COMPOSITIONS CONTAINING AN ALKYLATED SILICONE ACRYLATE COPOLYMER

(71) Applicant: L'ORÉAL, Paris (FR)

(72) Inventors: Rita Jaky El-Khouri, Morristown, NJ (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/983,347

(22) Filed: Dec. 29, 2015

(65) Prior Publication Data

US 2017/0181957 A1 Jun. 29, 2017

(51) Int. Cl.
| | |
|---|---|
| *A61K 8/895* | (2006.01) |
| *A61K 8/02* | (2006.01) |
| *A61K 8/06* | (2006.01) |
| *A61K 8/26* | (2006.01) |
| *A61K 8/81* | (2006.01) |
| *A61K 8/92* | (2006.01) |
| *A61Q 1/04* | (2006.01) |

(52) U.S. Cl.
CPC ............ *A61K 8/895* (2013.01); *A61K 8/0229* (2013.01); *A61K 8/06* (2013.01); *A61K 8/26* (2013.01); *A61K 8/8152* (2013.01); *A61K 8/92* (2013.01); *A61Q 1/04* (2013.01); *A61K 2800/42* (2013.01); *A61K 2800/48* (2013.01); *A61K 2800/591* (2013.01)

(58) Field of Classification Search
CPC .... A61K 8/0229; A61K 8/895; A61K 8/8152; A61K 8/26; A61K 8/06; A61K 8/92; A61K 2800/591; A61K 2800/48; A61K 2800/42; A61Q 1/04
See application file for complete search history.

(56) References Cited

U.S. PATENT DOCUMENTS

| | | | |
|---|---|---|---|
| 5,266,321 A | 11/1993 | Shukuzaki et al. | |
| 6,338,839 B1 | 1/2002 | Auguste et al. | |
| 9,078,820 B2 | 7/2015 | Moneuze et al. | |
| 2002/0028223 A1* | 3/2002 | Vatter | A61K 8/31 424/401 |
| 2004/0126350 A1 | 7/2004 | Blin et al. | |
| 2004/0170586 A1 | 9/2004 | Ferrari et al. | |
| 2007/0149703 A1* | 6/2007 | Caprasse | A61K 8/06 524/588 |
| 2011/0117041 A1* | 5/2011 | Chantal | A61K 8/375 424/64 |
| 2014/0018508 A1* | 1/2014 | Masubuchi | C08F 290/068 526/279 |

FOREIGN PATENT DOCUMENTS

| | | |
|---|---|---|
| EP | 0295886 | 12/1988 |
| JP | 2704730 | * 1/1998 |
| WO | WO03/042221 | 5/2003 |

OTHER PUBLICATIONS

Suzuki et al., JP 2704730, published: Jan. 26, 1998; English machine translation obtained on Nov. 27, 2016.*
International Preliminary Report on Patentability and Written Opinion dated Jul. 12, 2018 in PCT/US2016/061038, 8 pages.

* cited by examiner

*Primary Examiner* — Johann R Richter
*Assistant Examiner* — Genevieve S Alley
(74) *Attorney, Agent, or Firm* — Oblon, McClelland, Maier & Neustadt, L.L.P.

(57) ABSTRACT

The invention relates to a composition, especially a cosmetic composition, comprising at least one alkylated silicone acrylate copolymer, as well as to methods of using such compositions.

19 Claims, No Drawings

COMPOSITIONS CONTAINING AN ALKYLATED SILICONE ACRYLATE COPOLYMER

FIELD OF THE INVENTION

The present invention relates to compositions comprising at least one alkylated silicone acrylate copolymer. Among other improved or beneficial properties, these compositions have surprisingly good gloss, flake-resistance and/or transfer-resistance properties.

DISCUSSION OF THE BACKGROUND

Many cosmetic compositions, including pigmented cosmetics such as foundations and lipsticks, have been formulated in an attempt to possess long wearing properties upon application. Unfortunately, many of these compositions do not generally possess good long-wear/transfer-resistance properties, good gloss properties and good application properties.

For example, commercial products containing silicone resins such as MQ resins are known. Such products are known to provide good long wear properties and/or transfer-resistance. However, such compositions possess poor application properties and poor feel upon application (owing to the film formed by the MQ resin). Also, commercial products containing silicone acrylates are known. Generally speaking, however, such products are flaky (flake off after application). In addition, when film formation occurs in such products, there is very low to no gloss or shine. Attempts to address flakiness generally include blending silicone acrylates with a plasticizer, which has an adverse effect on the transfer of the product. Thus, there remains a need for improved cosmetic compositions having improved cosmetic properties, particularly good gloss, flake-resistance and/or transfer-resistance upon application. For example, there is a need for new compositions, particularly lipsticks, that have good gloss, flake-resistance and transfer-resistance all in the same composition. Currently, to possess all of these properties, it is generally necessary to use multiple products such as a basecoat having good wear properties and a topcoat having good gloss properties Accordingly, one aspect of the present invention is a care and/or makeup and/or treatment composition for keratinous materials which has good cosmetic properties such as, for example, good gloss, flake-resistance and/or transfer-resistance upon application, and in particular a composition which has all of these properties.

SUMMARY OF THE INVENTION

The present invention relates to compositions comprising at least one alkylated silicone acrylate copolymer. Preferably, the compositions are anhydrous.

The present invention also relates to colored compositions comprising at least one coloring agent and at least one alkylated silicone acrylate copolymer. Such colored compositions can be, for example, cosmetic compositions such as lip compositions (for example, lipstick or liquid lip compositions) or foundations. Preferably, the compositions are anhydrous.

The present invention also relates to methods of treating, caring for and/or making up keratinous material (for example, skin or lips) by applying compositions of the present invention to the keratinous material in an amount sufficient to treat, care for and/or make up the keratinous material.

The present invention also relates to methods of enhancing the appearance of keratinous material (for example, skin or lips) by applying compositions of the present invention to the keratinous material in an amount sufficient to enhance the appearance of the keratinous material.

The present invention further relates to compositions having improved cosmetic properties such as, for example, increased good gloss, flake-resistance and/or transfer-resistance properties.

The present invention also relates to methods of improving the good gloss, flake-resistance and/or transfer-resistance properties of a composition comprising adding to a composition (for example, a lip composition) at least one alkylated silicone acrylate copolymer in an amount sufficient to improve one or more of these properties.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to lips followed by rubbing a material, for example, a sheet of paper, against the lips after expiration of a certain amount of time following application, such as 2 minutes after application. Similarly, transfer resistance of a composition may be evaluated by the amount of product transferred from a wearer to any other substrate, such as transfer from the lips of an individual to a collar when putting on clothing after the expiration of a certain amount of time following application of the composition to the lips. The amount of composition transferred to the substrate (e.g., collar, or paper) may then be evaluated and compared. For example, a composition may be transfer resistant if a majority of the product is left on the wearer's lips. Further, the amount transferred may be compared with that transferred by other compositions, such as commercially available compositions. In a preferred embodiment of the present invention, little or no composition is transferred to the substrate from the lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to lips and evaluating the color of the composition after an extended period of time. For example, the color of a composition may be evaluated immediately following application to lips and these characteristics may then be re-evaluated and compared after a certain amount of time. Further, these characteristics may be evaluated with respect to other compositions, such as commercially available compositions.

"Flake-Resistance" as used herein refers to the quality exhibited by compositions that do not readily flake or peel off after application. Flake-resistance may be evaluated by any method known in the art for evaluating such. For example, samples to be tested for flake-resistance can be deposited onto a pliable or stretchable surface such as a bioskin substrate. After drying, the substrates and samples on the substrates are stretched in one direction, preferably a single time. Then, it can be determined how much of the sample is caused to flake by the stretching. For example, a rating scale such as a scale of 1-3 can be used to assess the degree of sample flaking, in which 1 is essentially no flaking, 2 some flaking, and 3 is essentially completely flaking off.

"Gloss" in compositions as used herein refers to compositions having with an average gloss, measured at 20°, of greater than or equal to 35, for example 40, preferably 45, 55, 60 or 65 out of 100, including all ranges and subranges therebetween such as 35-65, 40-65, etc., and/or an average gloss, measured at 60°, of greater than or equal to 65, 70, 75 or 80 out of 100, including all ranges and subranges therebetween such as 65-80, 65-75, etc.

The term "average gloss" denotes the gloss as it can be measured using a gloss meter, for example by spreading a layer of the composition to be tested, between 50 μm and 500 μm in thickness, on a Leneta contrast card of reference Form 1A Penopac using an automatic spreader. The layer covers at least the white background of the card. The deposit is left to dry for 24 hours at a temperature of 25° C., and then the gloss is measured at 20° on the white and/or black background using a Byk Gardner gloss meter of reference microTRI-GLOSS. This measurement (of between 0 and 100) is repeated at least three times, and the average gloss is the average of the at least three measurements carried out.

The average gloss at 60° is measured in a similar manner, the measurement being carried out at 60° rather than 20°.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

The cosmetic compositions and methods of the present invention can comprise, consist of, or consist essentially of the essential elements and limitations of the invention described herein, as well as any additional or optional ingredients, components, or limitations described herein or otherwise useful in personal care.

Alkylated Silicone Acrylate Copolymer

According to the present invention, compositions comprising at least one alkylated silicone acrylate copolymer are provided. Suitable alkylated silicone acrylate copolymers in accordance with the present invention are disclosed, for example, in Japanese patent 2704730, the entire contents of which is hereby incorporated by reference. Examples of commercially available copolymers of the present invention include those from ShinEtsu having the designation x-22-8337E, x-22-8337C, and x-22-8338C.

According to preferred embodiments of the present invention, the alkylated silicone acrylate copolymer has glass transition temperature(s) below body temperature (37° C.), preferably below room temperature (25° C.), preferably below 20° C., preferably below 15° C., and preferably below 10° C., with the temperature being preferably above 0° C. For example, the glass transition temperature(s) is preferably in the range 0° C. to 20° C., preferably 2.5° C. to 15° C., and preferably 3° C. to 10° C., including all ranges and subranges therebetween.

Suitable alkylated silicone acrylate copolymers include copolymers having a (meth)acrylate backbone and pendant alkyl groups. According to preferred embodiments, the pendant alkyl groups contain from 1 to 30 carbon atoms, preferably from 1 to 25 carbon atoms, preferably from 1 to 20 carbon atoms including all ranges and subranges therebetween.

The pendant alkyl groups can be substituted or unsubstituted. If substituted, preferable substitution groups include alkoxy such as glyceryl, ethoxy ($CH_2CH_2O$) or propoxy ($CH_2CH_2CH_2O$), hydroxy (OH), hydroxyalkyl such as, for example, hydroxymethyl, hydroxyethyl, hydroxypropyl, hydroxybutyl, etc., and perfluro alkyl. Preferably, the alkoxy, hydroxyalkyl and the perfluoro alkyl substitutions, if present, contain alkyl portions containing from 1 to 30 carbon atoms, preferably 1 to 18 carbon atoms, including all ranges and subranges therebetween.

Accordingly to preferred embodiments, the alkylated silicone acrylate copolymers can have one or more different pendant alkyl groups such as, for example, one pendant alkyl group, two pendant alkyl groups, three pendant alkyl groups, four pendant alkyl groups and five pendant alkyl groups. For example, an alkylated silicone acrylate copolymer of the present invention can have three pendant alkyl groups such as a pendant methyl group, a pendant ethyl group and a pendant propyl group.

According to preferred embodiments, the silicone portion of the alkylated silicone acrylate copolymer is substituted or unsubstituted polydimethylsiloxane. If substituted, preferable substitution groups include alkoxy such as glyceryl, ethoxy ($CH_2CH_2O$) or propoxy ($CH_2CH_2CH_2O$), hydroxy (OH), hydroxyalkyl such as, for example, hydroxymethyl, hydroxyethyl, hydroxypropyl, hydroxybutyl, etc., and perfluoro alkyl. Preferably, the alkoxy, hydroxyalkyl and the perfluoro alkyl substitutions, if present, contain alkyl portions containing from 1 to 8 carbon atoms, preferably 2 to 4 carbon atoms.

As explained more fully in Japanese patent 2704730, the alkylated silicone acrylate copolymers of the present invention can be made by free radical polymerization of the alkyl (meth)acrylated portion and/or the silicone portion of the copolymer. For example, the silicone portion can have polymerizability in one end as shown by the following general formula (1):

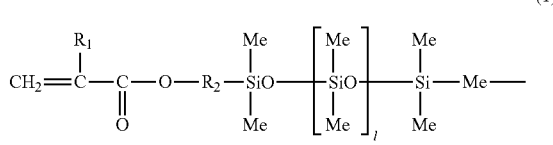

(1)

where Me is a methyl group, $R_1$: is a methyl group or a hydrogen atom, and $R_2$ is a hydrocarbon group optionally containing an ether bond.

And, for example, the alkylated (meth)acrylated portion may have a polymerizable unsaturated bond. Examples of alkylated (meth)acrylated portions include methyl (meth) acrylate, ethyl (meth)acrylate, n-butyl (meth)acrylate, alkyl (meth)acrylate, such as 2-ethylhexyl (meth)acrylate, hydroxyalkyl (meth)acrylate, such as 2-hydroxyethyl (meth) acrylate and 2-hydroxypropyl (meth)acrylate, and perfloro alkyl (meth) acrylate.

In the composition of the present invention, the alkylated silicone acrylate copolymer(s) is/are preferably present in an amount of from about 1% to about 50% by weight, preferably from 5% to 50% by weight, preferably from 10% to 45% by weight, and preferably from 20% to 40% by weight of the total weight of the composition, including all ranges and subranges therebetween.

According to preferred embodiments the combination of the alkylated silicone acrylate copolymer and silicone emulsifier results in a film having an elastic modulus at 37° C. below $10^8$ Pa, preferably below $10^7$ Pa and preferably below $10^6$ Pa.

Oil Phase

According to the present invention, compositions comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils. According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |

TABLE 2-continued

| Compound | Flash Point (° C.) |
|---|---|
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7\geq10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to certain embodiments of the present invention, the compositions of the present invention comprise at least one silicone oil. Suitable examples of such silicone oils include, but are not limited to, non-volatile silicone fluids such as, for example, polyalkyl (aryl) siloxanes. Suitable polyalkyl siloxanes include, but are not limited to, polydimethyl siloxanes, which have the CTFA designation dimethicone, polydiethyl siloxane, phenyl trimethicone, trimethyl pentaphenyl trisiloxane, phenydimethicone, phenyltrimethylsiloxydiphenylsiloxane, diphenyldimethicone, and diphenylmethyldiphenyltrisiloxane and those siloxanes disclosed in U.S. patent application publication no. 2004/0126350, the entire disclosure of which is hereby incorporated by reference. Specific examples of suitable high viscosity silicone oils include, but are not limited to, 15 M 30 from PCR (500 cSt) or Belsil PDM 1000 (1 000 cSt) from Wacker and Dow Corning 200 (350 cSt) (the values in parenthesis represent viscosities at 25° C.).

According to preferred embodiments, the at least one oil is present in the compositions of the present invention in an amount ranging from about 5 to about 60% by weight, more preferably from about 10 to about 50% by weight, and most preferably from about 15 to about 35% by weight, based on the total weight of the composition, including all ranges and subranges within these ranges.

According to particularly preferred embodiments, the compositions of the present invention, at least one volatile oil and at least one non-volatile oil are present. In accordance with these preferred embodiments, the at least one volatile oil is present in the compositions of the present invention in an amount ranging from about 5 to about 50% by weight, preferably from about 10 to about 40% by weight, and preferably from about 12 to about 37% by weight, based on the total weight of the composition, including all ranges and subranges within these ranges, and the at least one non-volatile oil is present in the compositions of the present invention in an amount ranging from about 10 to about 50% by weight, preferably from about 12 to about 45% by weight, and preferably from about 15 to about 40% by weight, based on the total weight of the composition, including all ranges and subranges within these ranges.

According to preferred embodiments of the present invention, the compositions of the present invention comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application 2007/0149703, the entire contents of which is hereby incorporated by reference, with a particular example being C30-C45 alkyldimethylsilyl polypropylsilsesquioxane; and mixtures thereof.

According to particularly preferred embodiments of the present invention, the compositions of the present invention further include at least one long-Chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

If present, the wax or waxes may be present in an amount ranging from 0.1 to 30% by weight relative to the total weight of the composition, for example from 0.2 to 20%, and for example from 0.3 to 10%, including all ranges and subranges therebetween.

Coloring Agents

According to preferred embodiments of the present invention, compositions further comprising at least one coloring agent are provided. Preferably, such colored compositions can be cosmetic compositions such as, for example, lip compositions (for example, lipstick) or foundations.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

In particular, among the gelling agents that may be used, mention may be made of lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to $C_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

Also, regarding silicone elastomers that may be used, the term "elastomer" is understood to mean a flexible and deformable solid material having visco-elastic properties and in particular the consistency of a sponge or of a flexible sphere. Its modulus of elasticity is such that this material withstands deformation and has a limited ability to expand and to contract. This material is capable of returning to its original shape after it has been stretched. This elastomer is formed of high molecular weight polymer chains, the mobility of which is limited by a uniform network of crosslinking points. The elastomers used in the composition according to the invention are preferably partially or completely crosslinked. They are in the form of particles. In particular, the particles of elastomer have a size ranging from 0.1 to 500 μm, preferably from 3 to 200 μm and preferably from 3 to 50 μm. These particles may have any shape and, for example, may be spherical, flat or amorphous. Suitable examples of silicone elastomers include, for example, those sold under the names KSG 6 by Shin-Etsu; Trefil E-505C or Trefil E-506C by Dow Corning; Gransil (SR-CYC, SR DMF10, SR-DC556) by Grant Industries, or those sold in the form of gels that are already formed: KSG 15, KSG 16, KSG 17, KSG 18, KSG 26A, KSG 26B, KSG-31, KSG-32, KSG-33, KSG-41, KSG-42, KSG-43 and KSG-44 from Shin-Etsu; Gransil SR 5CYC gel, Gransil SR DMF 10 gel, Gransil SR DC556 gel and Gransil RPC from Grant Industries; 1229-02-167 and 1229-02-168 from General Electric.

Other examples include silicone elastomers bearing the INCI name dimethicone/vinyldimethicone copolymer (or polysilicone-11), as well as the mixture of crosslinked organopolysiloxane/cyclopentasiloxane or a mixture of crosslinked organopolysiloxane/cyclohexasiloxane such as, for example, Gransil RPS D5 or Gransil RPS D6 from Grant Industries. Mention may also be made of the elastomers sold under the references DC 9040, DC 9041, DC 9509, DC 9505 and DC 9506 by Dow Corning.

Finally, suitable elastomers are disclosed in EP-A-0 295 886, U.S. Pat. Nos. 5,266,321, and 9,078,820, the entire contents of all of which are hereby incorporated by reference A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin and lips by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratin material in an amount sufficient to treat, care for and/or make up the keratinous material, to cover or hide defects associated with keratinous material, skin imperfections or discolorations, or to enhance the appearance of keratinous material. The compositions may be applied to the desired area as needed, preferably once or twice daily, more preferably once daily and then preferably allowed to dry before subjecting to contact such as with clothing or other objects (for example, a glass or a topcoat).

According to a preferred embodiment of the present invention, compositions having improved cosmetic properties such as, for example, improved gloss, flake-resistance and/or transfer-resistance properties are provided.

According to other embodiments of the present invention, methods of improving gloss, flake-resistance and/or transfer-resistance properties of a composition, comprising adding at least one alkylated silicone acrylate copolymer in an amount sufficient to improve shine and/or improve long-wear properties are provided. According to further embodiments of the present invention, methods of improving the gloss, flake-resistance and/or transfer-resistance of a composition, preferably a makeup compositions such as a foundation or lip composition, comprising adding at least one alkylated silicone acrylate copolymer to the composition are provided. Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1: Testing Protocols

The following testing protocols were used and are illustrative of methods that can be used in accordance with the present invention:

Flake Testing:

Samples were tested for their flake resistant properties. Samples were deposited onto the bioskin surface using a 3 mil draw down bar for liquid samples. The samples were allowed to dry for 1-2 hours for liquid samples. For stick samples, the product was deposited on bioskin using 10 strokes within a 2×3 cm rectangular area on the bioskin and dried for 20 minutes to 1 hour. Then, the samples were stretched in one direction, one time. A rating scale from 1-3 was used to assess the degree of sample flaking, in which 1 was no flaking, 2 was somewhat flaking, and 3 was completely flaking off.

Gloss Testing:

Samples were evaluated for their gloss value using a gloss meter. Sample films were prepared by using a 6 mil drawdown bar to deposit a film onto contrast paper. Films were allowed to dry for six hours and then were evaluated for their gloss values. From the values captured, the 20 degree value was reported.

Transfer-Resistance Testing:

The solid stick samples were applied on a slab of bioskin using five strokes. The sample was allowed to dry for up to 20 minutes. Following the dry time, the sample was pressed manually with a kimwipe, and a transfer score was given in which 1 was no transfer, 2 was some transfer, and 3 was high transfer Example 2—Composition Preparation The following preparation methods were used and are illustrative of methods that can be used in accordance with the present invention:

Liquid Compositions:

Polymer solutions and a portion of isododecane were blended under high shear at elevated temperature until all materials were completely blended. Once the mixture became homogenous, pigment solution, mica and the final amount of isododecane was added to the mixture and blended until homogenous.

Solid Compositions:

Polymer solutions, wax, and a portion of isododecane were blended under high shear at 95° C. until all materials were completely blended. The solution temperature was brought down to 65° C. and residual solvent, pigments, fillers were added to the mixture. Once the mixture became homogenous the formula was poured into a mold, and chilled. The samples were de-molded and placed within components.

Example 3—Sample Liquid Compositions and Testing Results

1. Inventive liquid composition 1 and 2 were prepared, and the flake resistance of these compositions were compared to commercially available products to determine relative wear properties. Invention compositions 1 and 2 had similar flake resistance properties than the commercially-available comparative products but better than the control 3 in which a different silicone acrylate is used. The inventive samples 1 and 2 had measured gloss values greater than 10 at the 20° angle.

|  | Inventive 1 | Inventive 2 | Comparative 3 |
|---|---|---|---|
| *Silicone Acrylate 50% Polymer Solution in Isododecane *ShinEtsu x-22-8337E | 80 | 50 | 0 |
| Silicone Acrylate 40% Solution in Isododecane *Shinetsu KP550 | 0 | 0 | 75 |
| Red 7 | 1.214 | 1.214 | 1.214 |
| Bentone Gel | 10 | 10 | 10 |
| Isododecane | QS | QS | QS |
| Total | 100 | 100 | 100 |
| Flaking Test | 1 | 1 | 3 |
| 20 Degree Gloss Value | 51.1 ± 1.8 | 10.90 ± 0.4 | 3.3 ± 0.0 |

|  | Comparative 4 Silicone Resin/ Silicone Nylon copolymer Technology Basecoat | Comparative 5 Silicone Resin/ Silicone Nylon copolymer Technology Basecoat &Topcoat | Comparative 6 Silicone Resin/ Dimethicone Technology |
|---|---|---|---|
| *Silicone Acrylate 50% Polymer Solution in Isododecane *ShinEtsu x-22-8337E | Two Step Product Comparative 3 is the first step Comparative 4 is both steps | | Single Step Product |
| Silicone Acrylate 40% Solution in Isododecane *Shinetsu KP550 | | | |
| Red 7 | | | |
| Bentone Gel | | | |
| Isododecane | | | |
| Total | | | |
| Flaking Test | 1 | 1 | 1 |
| 20 Degree Gloss Value | 1.3 ± 0.0 | 39.0 ± 4.6 | 0.5 ± 0.0 |

Example 4—Sample Solid Compositions and Testing Results

Inventive solid composition 6 was prepared, and the flake resistance and transfer resistance of this composition were compared to commercially available products to determine relative wear properties. Invention composition 6 had better wear properties than the commercially-available comparative stick products.

|  | Inventive 6 % | Comparative 7 Silicon Resin/ Dimethicone Technology | Comparative 8 Silicone Resin Technology |
|---|---|---|---|
| Silicone Acrylate 50% Polymer solution in isododecane* | 50 | | |
| Red 7 | 4.3 | | |
| Filler | 3 | | |
| Waxes | 14 | | |
| Isododecane (QSP) | 28.7 | | |
| Total | 100.0 | | |
| % Active Polymer | 25% | | |
| Flake Resistance Testing | 1 | 1 | 1 |
| Transfer Resistance Testing | 1 | 3 | 2 |

What is claimed is:

1. A liquid lip composition, comprising:
   at least one alkylated silicone acrylate copolymer in an amount of from about 20% to about 50% by weight based on a total weight of the composition;

at least one coloring agent, and at least one non-volatile oil in an amount of from about 5% to 60% by weight based on the total weight of the composition, wherein the composition is anhydrous and has a gloss value at 20° angle of 10 or greater.

2. The composition of claim 1, further comprising at least one volatile oil.

3. The composition of claim 2, wherein:

the non-volatile oil is present in an amount of from about 10% to about 50% by weight based on the total weight of the composition, and the volatile oil is present in an amount of from about 5% to about 50% by weight based on the total weight of the composition.

4. The composition of claim 2, wherein:

the non-volatile oil is present in an amount of from about 15% to about 40% by weight based on the total weight of the composition, and the volatile oil is present in an amount of from about 12% to about 37% by weight based on the total weight of the composition.

5. The composition of claim 1, wherein the alkylated silicone acrylate copolymer has a glass transition temperature in the range of 0° C. to 37° C.

6. The composition of claim 1, further comprising at least one thickening agent.

7. The composition of claim 1, further comprising at least one elastomer.

8. The composition according to claim 7, wherein the elastomer is partially or completely crosslinked and in a form of particles having a size ranging from 3 to 200 μm.

9. The composition of claim 1, further comprising at least one clay.

10. The composition of claim 1, wherein the alkylated silicone acrylate copolymer results in a film having an elastic modulus at 37° C. below 106 Pa.

11. The composition of claim 1, wherein the alkylated silicone acrylate copolymer comprises a (meth)acrylate backbone with pendant alkyl groups, and a substituted or unsubstituted poly dimethylsiloxane.

12. The composition of claim 1, wherein the coloring agent is present in a concentration of from 0.5% to 40% by weight based on the total weight of the composition.

13. A solid composition comprising at least one alkylated silicone acrylate copolymer, at least one silicone wax, and at least one coloring agent, wherein the alkylated silicone acrylate copolymer is present in the composition in an amount of from about 20% to about 50% by weight of the total weight of the composition.

14. The composition of claim 13, wherein the silicone wax is C30-C45 alkyldimethylsilyl polypropylsilsesquioxane.

15. The composition of claim 13, in the form of a stick.

16. The composition of claim 13, wherein the silicon wax is present in an amount ranging from 0.3% to 10% by weight based on the total weight of the composition.

17. The composition of claim 13, wherein the coloring agent is present in a concentration of from 0.5% to 40% by weight based on the total weight of the composition.

18. The composition according to claim 13, further comprising an elastomer, wherein the elastomer is partially or completely crosslinked and in a form of particles having a size ranging from 3 to 200 μm.

19. A method of making up lips comprising applying the composition of claim 1 to the lips.

* * * * *

UNITED STATES PATENT AND TRADEMARK OFFICE
CERTIFICATE OF CORRECTION

PATENT NO. : 10,426,722 B2
APPLICATION NO. : 14/983347
DATED : October 1, 2019
INVENTOR(S) : Rita Jaky El-Khouri et al.

Page 1 of 1

It is certified that error appears in the above-identified patent and that said Letters Patent is hereby corrected as shown below:

In the Claims

In Column 16, Line 3, Claim 10, "106" should read -- $10^6$ --.

In Column 16, Line 7, Claim 11, "poly dimethylsiloxane" should read -- polydimethylsiloxane --.

Signed and Sealed this
Seventh Day of April, 2020

Andrei Iancu
*Director of the United States Patent and Trademark Office*